(12) United States Patent
Patel

(10) Patent No.: US 10,314,309 B2
(45) Date of Patent: Jun. 11, 2019

(54) INORGANIC COATING AND COMPOSITION

(71) Applicant: Latitude 18, Inc., Wilson, NC (US)

(72) Inventor: Sameerkumar Vasantlal Patel, Raleigh, NC (US)

(73) Assignee: LATITUDE 18, INC., Sims, NC (US)

( * ) Notice: Subject to any disclaimer, the term of this patent is extended or adjusted under 35 U.S.C. 154(b) by 311 days.

(21) Appl. No.: 14/768,125

(22) PCT Filed: Feb. 15, 2013

(86) PCT No.: PCT/US2013/026401
§ 371 (c)(1),
(2) Date: Aug. 14, 2015

(87) PCT Pub. No.: WO2014/126584
PCT Pub. Date: Aug. 21, 2014

(65) Prior Publication Data
US 2015/0366213 A1 Dec. 24, 2015

(51) Int. Cl.
| | | |
|---|---|---|
| *A01N 59/06* | (2006.01) | |
| *C23C 24/02* | (2006.01) | |
| *C23C 18/12* | (2006.01) | |
| *A01N 59/16* | (2006.01) | |
| *A01N 59/20* | (2006.01) | |
| *B05D 1/02* | (2006.01) | |
| *B05D 1/28* | (2006.01) | |
| *B05D 1/42* | (2006.01) | |
| *C09D 1/00* | (2006.01) | |
| *C09D 5/14* | (2006.01) | |
| *C09D 5/16* | (2006.01) | |

(52) U.S. Cl.
CPC ............ *A01N 59/06* (2013.01); *A01N 59/16* (2013.01); *A01N 59/20* (2013.01); *B05D 1/02* (2013.01); *B05D 1/28* (2013.01); *B05D 1/42* (2013.01); *C09D 1/00* (2013.01); *C09D 5/14* (2013.01); *C09D 5/16* (2013.01); *C23C 18/1212* (2013.01); *C23C 18/1241* (2013.01); *C23C 18/1245* (2013.01); *C23C 24/02* (2013.01)

(58) Field of Classification Search
None
See application file for complete search history.

(56) References Cited

U.S. PATENT DOCUMENTS

| | | | | |
|---|---|---|---|---|
| 3,895,956 A | * | 7/1975 | Yoshida | C04B 28/24 106/2 |
| 3,955,985 A | * | 5/1976 | Bosch | C04B 20/1051 106/2 |
| 4,999,250 A | | 3/1991 | Richardson et al. | |
| 6,194,357 B1 | | 2/2001 | Murata et al. | |
| 2004/0037964 A1 | * | 2/2004 | Davies | C09D 1/00 427/397.8 |
| 2008/0026183 A1 | | 1/2008 | Vanpoulle et al. | |
| 2008/0221263 A1 | | 9/2008 | Kanagasabapathy et al. | |
| 2008/0311411 A1 | | 12/2008 | Balaguru | |
| 2011/0143154 A1 | * | 6/2011 | Wagh | C09D 5/08 428/472.3 |
| 2011/0143910 A1 | | 6/2011 | Wagh et al. | |
| 2011/0308423 A1 | * | 12/2011 | Friedel | C04B 41/009 106/2 |

FOREIGN PATENT DOCUMENTS

| | | |
|---|---|---|
| CN | 102770583 A | 11/2012 |
| CN | 102781871 A | 11/2012 |

OTHER PUBLICATIONS

EPO; Extended European Search Report for European Application No. 13875160.7 dated Feb. 15, 2017, 10 pages.
The International Bureau of WIPO; International Preliminary Report on Patentability for International Application No. PCT/US2013/026401 dated Aug. 27, 2015, 11 Pages.
Korean Intellectual Property Office; International Search Report for International Application No. PCT/US2013/026401 dated Oct. 25, 2013, 15 pages.
SIPO; Office Action for Chinese Application No. 201380075680.7 dated Dec. 5, 2016, 11 pages.
EPO; Search Report for European Application No. 13875160.7 dated Dec. 10, 2016, 7 pages.

* cited by examiner

*Primary Examiner* — Nathan T Leong
(74) *Attorney, Agent, or Firm* — Christopher J. Knors; Moore & Van Allen PLLC

(57) ABSTRACT

This disclosure relates to basic inorganic compositions. Methods of providing antifungal/antibacterial resistance and/or hydrophobicity and/or corrosion resistance by coating surfaces with the basic inorganic compositions are provided. In another aspect, a silicate composition comprising at least one alkali earth metal; and a Group IV element of silicon, germanium, tin, or lead having at least one hydrocarbon moiety covalently bonded thereto is provided.

8 Claims, No Drawings

INORGANIC COATING AND COMPOSITION

CROSS-REFERENCE TO RELATED APPLICATIONS

This application is filed under the provisions of 35 U.S.C. § 371 and claims the benefit of International Patent Application No. PCT/US2013/026401, filed on Feb. 15, 2013, which is hereby incorporated by reference in its entirety.

TECHNICAL FIELD

This disclosure relates to inorganic coatings, specifically, the composition, manufacture, and method of providing resistance to mold and/or bacterial growth and/or waterproofing and/or corrosion protection to corrodible metal surfaces. The composition comprises at least one sparingly soluble basic metal oxide or metal hydroxide, one or more sparingly soluble inorganic silicates, and a basic inorganic salt.

BACKGROUND

Providing bacterial and/or mold resistance to metallic and non-metallic surfaces, without the use of fungicidal and bactericidal chemicals in the form of coatings has proven elusive. Typically, one or more fungicides and bactericides are included in the pre-set formulation in the desire to have them bloom or migrate to the surface upon or after setting. Such techniques result in the dissipation of the fungicidal/bactericidal properties over time and further require using an excess of such additives. Moreover, the use of specific fungicides and bactericides or classes of fungicides and bactericides ultimately results in resistant strains of these organisms. Providing waterproofing to inorganic coatings has also proven elusive. Providing both waterproofing and bacterial and/or mold resistance coatings has proven even more elusive.

Otherwise basic substances and surfaces, or media of high pH is at least partially effective for measurable control of certain microbes. "Water-glass" or soluble silicates, for example, sodium or potassium silicate, and/or the sodium or potassium salt of silicic acid salt, or disodium metasilicate, which can be basic depending on SiO2:Na2O ratios, are sometimes used as an anti-microbial surface treatment when formulated as a silicate mineral paint having the water glass as a binder. However, such silicate mineral paints are typically prepared as coating formulations using a weak acid, e.g., carbonate salt (for stability), thus rendering the solution and the subsequent coating to a pH of less than 9, and they need a fixative to seal the silicate to the substrate.

SUMMARY

In a first embodiment, a composition is provided. The composition comprising: at least one aqueous sparingly soluble metal oxide/hydroxide; at least one sparingly soluble inorganic mineral; and at least one soluble basic inorganic salt.

In one aspect, the at least one sparingly soluble metal oxide/hydroxide is at least one of magnesium oxide, magnesium hydroxide, calcium oxide, and calcium hydroxide. In other aspects, the at least one sparingly soluble metal oxide/hydroxide is at least one of barium oxide, zinc oxide, copper oxide, and hydroxides thereof.

In one aspect, alone or in combination with any of the previous aspects, the at least one sparingly soluble inorganic mineral is one or more of an inorganic mineral silicate, wollastonite, talc, amorphous magnesium silicate, amorphous calcium silicate, diatomaceous earth, aluminosilicate, olivine, calcined kaolin, mullite, colloidal silica, silicon dioxide, and amorphous silicon dioxide.

In one aspect, alone or in combination with any of the previous aspects, the at least one soluble basic inorganic salt is one or more of an alkali metal or alkali earth metal salt of one of a phosphate, or a silicate. In one aspect, alone or in combination with any of the previous aspects, the at least one soluble basic inorganic salt is one or more of an alkali metal or alkali earth metal hydroxide.

In one aspect, alone or in combination with any of the previous aspects, the composition further comprises at least one hydrophobic agent, wherein the hydrophobic agent is of the general formula (I) or (II) or (III) or (IV):

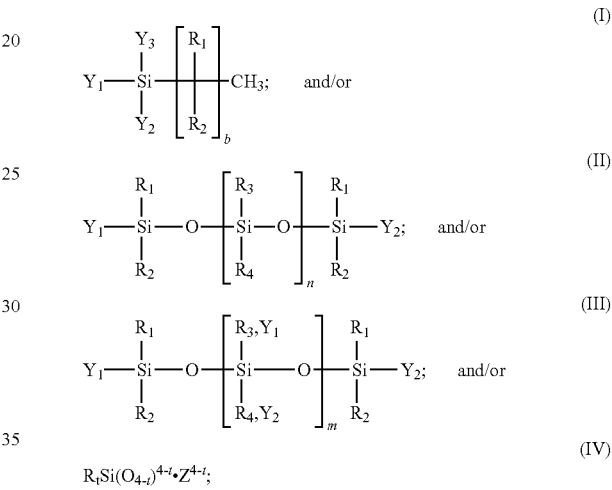

where:
$R_1$, $R_2$, $R_3$, and $R_4$ are, independently, hydrogen, $C_{1-20}$ alkyl, phenyl, aryl; where alkyl includes straight-chain, branched, cyclic or acylic alkyl, or haloalkyl;

$Y_1$, $Y_2$, and $Y_3$ is, independently, hydroxyl, $C_{1-4}$ alkoxy, phenoxide, or halogen; or, $Y_1$, $Y_2$, and $Y_3$ is, independently, an alkali metal salt, an ammonium salt, an alkylammonium salt, a phenylammonium salt, or an alklyphenylammonium salt of Si—OH;

b is 0-21; n is greater than 1,000 to 1,000,000;

m is 0-1,000; and

Z is sodium or potassium.

In one aspect, alone or in combination with any of the previous aspects, the organosiliconate is a potassium salt, e.g., a mono-, di-, or tri-alkyl siliconate.

In a second embodiment, method of preventing or reducing fungal or bacterial growth on a surface is provided. The method comprising: combining the composition of the first embodiment; contacting a surface with the combined composition, wherein the surface, after contacting, provides a basic environment of at least pH 9 to pH 14; and reducing or eliminating fungal or bacterial growth on the surface.

In one aspect, alone or in combination with any of the previous aspects, the surface is metal or non-metal. In one aspect, the surface is associated with a medical article, medical device, or structure.

In one aspect, alone or in combination with any of the previous aspects, the combining is performed with high shear.

In one aspect, alone or in combination with any of the previous aspects, the contacting is at least one of painting, brushing, troweling, and spraying.

In a third embodiment, method of preventing or reducing fungal or bacterial growth on a surface is provided. The method comprising: combining the precursor formulation of any of the previous embodiments or aspects; contacting a surface with the combined precursor formulation of any of the previous embodiments or aspects, wherein the surface, after contacting, provides a basic environment of at least pH 9 to pH 14; and preventing or reducing fungal or bacterial growth on the surface.

In one aspect, alone or in combination with any of the previous aspects, the at least one sparingly soluble metal oxide/hydroxide component is one or more of magnesium oxide, magnesium hydroxide, magnesium brine containing an effective amount of magnesium hydroxide, calcium oxide, and calcium hydroxide. In one aspect, the at least one sparingly soluble metal oxide/hydroxide component is at least one of barium oxide, zinc oxide, copper oxide, and hydroxides thereof.

In one aspect, alone or in combination with any of the previous aspects, the at least one soluble basic inorganic salt is one or more of an alkali metal or alkali earth metal salt of one of a phosphate, a silicate, or an alkylsiliconate. In one aspect, the at least one soluble basic inorganic salt is an organosiliconate or potassium salt of an organosiliconate. The at least one organosiliconate can be a mono-, di-, or tri-alkyl silicate. In one aspect, the at least one soluble basic inorganic salt is an alkali hydroxide or alkali earth hydroxide.

In one aspect, alone or in combination with any of the previous aspects, wherein the at least one soluble basic inorganic salt is potassium phosphate ($K_3PO_4$).

In one aspect, alone or in combination with any of the previous aspects, the hydrophobic agent is as described above for the first embodiment.

In one aspect, alone or in combination with any of the previous aspects, the at least one sparingly soluble inorganic mineral is one or more of wollastonite, talc, amorphous magnesium silicate, amorphous calcium silicate, diatomaceous earth, aluminosilicate, olivine, calcined kaolin, mullite, colloidal silica, silicon dioxide, and amorphous silicon dioxide.

In a fourth embodiment, method of preventing or reducing corrosion of a corrodible surface is provided. The method comprising: contacting a corrodible surface with the combined composition alone or in combination with any of the previous aspects thereof; and preventing or reducing corrosion on the corrodible surface.

In a fifth embodiment, a method of preventing or reducing attachment of Mollusca on a surface is provided. The method comprising: contacting a surface with the combined composition alone or in combination with any of the previous aspects thereof, wherein the surface, after contacting, provides a basic environment of at least pH 9; and preventing or reducing attachment of Mollusca on the surface. In one aspect, the Mollusca are fresh water mussels. In other aspect, the Mollusca are zebra mussel or quagga mussel.

In a sixth embodiment, a silicate composition is provided. The silicate composition comprising at least one alkali earth metal and at least one Group IV element of silicon, germanium, tin, or lead having at least one hydrocarbon moiety covalently bonded thereto. In a first aspect, the one or more hydrocarbon moiety is independently, $C_{1-20}$ alkyl, phenyl, aryl; where alkyl includes straight-chain, branched, or cyclic alkyl, haloalkyl (e.g. fluoro- or chloro alkyl). In one aspect, the at least one alkali earth metal is magnesium or calcium. In another aspect, alone or in combination with any of the previous aspects, the at least one Group IV element is silicon. In another aspect, alone or in combination with any of the previous aspects, the alkyl group is methyl, ethyl, butyl, sec-butyl, or t-butyl. In another aspect, alone or in combination with any of the previous aspects, the at least one alkali earth metal is magnesium and the at least one Group IV element is silicon, and the hydrocarbon is methyl.

BRIEF DESCRIPTION OF THE DRAWINGS

None

DETAILED DESCRIPTION

The present disclosure provides uniquely-suited, inorganic coatings having, among other things, hydrophobic properties that minimize or reduce the penetration of water and/or corrosion of metals, for example steels and iron and make it unnecessary to use alloys of steel or iron such as galvanized (zinc coated) compositions or chrome plated compositions.

In addition, the present disclosure provides inorganic coatings providing management of fungal/bacterial growth resistance.

As used herein phrases "sparingly soluble basic metal oxide and sparingly soluble basic metal hydroxide component" and "sparingly soluble basic component" and "sparingly soluble alkaline component" and "sparingly soluble alkaline precursor" are used interchangeably unless otherwise indicated. The phrases "sparingly soluble basic component" and "sparingly soluble alkaline component" and "sparingly soluble alkaline precursor" are inclusive of materials that are sparingly soluble, e.g., have low solubility product constants in aqueous media, e.g., e.g., solubility constants (Ksp) of at least $10^{-4}$, $10^{-5}$, $10^{-6}$, $10^{-7}$, $10^{-8}$, $10^{-9}$ or smaller. In one aspect, the solubility of the sparingly soluble basic component is less than about 0.1 moles/liter water. In one aspect, the phrases sparingly soluble basic metal oxide and sparingly soluble basic metal hydroxide component" and "sparingly soluble basic component" and "sparingly soluble alkaline component" and "sparingly soluble alkaline precursor" are exclusive of materials that are readily soluble, e.g., have high solubility product constants in aqueous media.

As used herein, the phrase "soluble basic inorganic salt" is inclusive of materials that are readily aqueous soluble, e.g., solubility constants (Ksp) of at least $10^{-3}$, $10^{-2}$ or greater, and have an aqueous pH of between about 10 to about 14, between about 11 to 14, between about 12 to 14, or between about 13 to 14. In one aspect, the solubility of the soluble basic inorganic salt is greater than about 0.1 moles/liter water, or greater than about 1 moles/liter water. "Basic inorganic salt of an inorganic acid" and "basic inorganic salt" include, by way of example, one or more of a bi-, and/or tri-alkali and/or alkali earth salt of phosphate ($PO_4^{-3}$), silicate ($SiO_4^{-3}$), alkyl silicate (alkyl-$SiO_3^{-3}$), or aluminate ($Al_2O_4^{-2}$). Other readily aqueous soluble basic inorganic salts, providing an aqueous pH of greater than 10, greater than 11, greater than 12, greater than 13, or an aqueous pH of between 10 and 14, can be used, for example, potassium hydroxide, and to a lesser extent, sodium hydroxide. The amount of basic inorganic salt present in an aqueous mixture of the sparingly soluble basic metal oxide/hydroxide component, alone or in combination with one or more sparingly aqueous soluble inorganic silicates, can be between about 1 weight percent to about 95 weight percent, or about 3-75 weight percent, or 5-50 weight percent solids.

As used herein, the phrase "aqueous mixture" refers to a combination of at least a quantity of water and at least one of the sparingly soluble basic component. For example, the aqueous mixture can contain mostly water and suspended, dispersed, or slurried components, and may also contain non-aqueous components such as alcohols and other solvents. Preferably, water is the major liquid phase. The amount of basic inorganic salt present in the aqueous mixture of the sparingly soluble basic metal oxide/hydroxide component, alone or in combination with one or more sparingly aqueous soluble inorganic silicates, can be between about 1 weight percent to about 75 weight percent, or about 2-50 weight percent, or 3-20 weight percent solids.

The amount of total solids (e.g., basic component and/or other solids) present in the aqueous mixture can be between 10 weight percent to about 95 weight percent, 35-90 weight percent, or 50-80 weight percent solids.

Examples of the basic inorganic coatings provided herein include a sparingly aqueous soluble metal oxide/hydroxide and sparingly aqueous soluble inorganic silicate with an aqueous soluble basic inorganic salt. Another example of the basic inorganic coatings provided herein include the combination of one or more metal oxide/hydroxide, one or more sparingly aqueous soluble inorganic mineral, e.g., a silicate, with one or more aqueous soluble basic inorganic salt.

In one example of the coatings disclosed herein, one or more metal oxide/hydroxide such as magnesium oxide/hydroxide and/or calcium oxide/hydroxide is combined with one or more sparingly soluble inorganic minerals, such as wollastonite, talc, amorphous magnesium silicate, amorphous calcium silicate, diatomaceous earth, silicon dioxide, calcined kaolin, colloidal silica, and amorphous silicon dioxide, and one or more of an aqueous soluble basic inorganic salt is added to provide stability to the mixture. In one aspect, the aqueous soluble basic inorganic salt comprises one or more of an alkali or alkali earth salt of a phosphate, a silicate, or an alkyl-, or aryl-siliconate. To be clear, the aqueous soluble basic inorganic salt of a silicate or an alkyl-, aryl-siliconate are not simply "fillers." The introduction of the alkyl-, aryl-siliconate salt provides for an inorganic-organic silicate composition with unique properties, namely, improved hydrophobicity, improved corrosion resistance, and improved microbial resistance. The inorganic-organic silicate composition can be applied from a precursor formulation as a coating to a substrate, or used as a monolithic form such as a floor, wall, or other architectural component.

These compositions are disclosed herein for providing coatings on steels, aluminum, and other metal or non-metal surfaces to reduce or eliminate fungal and/or bacterial growth thereon as well as provide hydrophobicity and/or corrosion protection. Additional agents can be added to the above, such as hydrolysable silicones, polysilicones, and combinations thereof, to impart additional properties to the coating, such as improved water resistance. The amount of the additional additives is such that the basic property of the coating is maintained, yet the water resistance is improved. Such loadings of additional additives can be about 1 to about 20 weight percent. In one aspect, the alkylsiliconate salt can be both the soluble basic inorganic salt and the hydrophobic agent.

In another example of the coatings disclosed herein, one or more metal oxide/hydroxide such as magnesium oxide/hydroxide and/or calcium oxide/hydroxide is combined with one or more sparingly soluble inorganic minerals, such as wollastonite, talc, amorphous magnesium silicate, amorphous calcium silicate, diatomaceous earth, silicon dioxide, calcined kaolin, colloidal silica, and amorphous silicon dioxide, and one or more of an aqueous soluble basic inorganic salt is added to form a precursor formulation. These compositions are disclosed herein for providing coatings on steels, aluminum, and other metal or non-metal surfaces to provide hydrophobicity, and/or reduce or eliminate fungal and/or bacterial growth thereon.

In one aspect, the present coatings provide an environment that is basic, for example, having a pH greater than what is biologically incompatible with the growth and/or colonization of bacteria and/or fungus (or mold). The pH of the environment can be adjusted to be greater than pH 9 to pH 14, between pH 9.5 and 14, between pH 10 and 13.5, or pH 10 to about 13. The environment of the coating includes the surface and the bulk thereof. The environment can be realized under ambient conditions of typical relative humidity or humid conditions. Such environments are effective in reducing or eliminating microbial growth and effective in at least partially neutralizing or killing one or more microbes that are presented to the surface of the coating.

In addition to reducing or eliminating fungal and/or bacterial growth, the coatings herein disclosed can be essentially water repellant and/or water impermeable. For example, a magnesium potassium phosphate and/or calcium potassium phosphate, calcium silicate (wollastonite) and/or magnesium silicate, and one or more alkylsilicates, such as potassium methylsiliconate, sodium methylsiliconate, potassium ethylsiliconate, or sodium ethylsiliconate, and the like can be used to provide a hydrophobic inorganic coating.

The above basic inorganic compositions can be used as monolithic forms, or as coatings that serve as a surface treatment for a metal or non-metal, a function it performs effectively with excellent adhesion and typically without primer layers. In contrast to the conventional methods of including chemicals for providing the fungal/bacterial resistance, the present coatings, in part due to the basic nature of the material, provides an environment that is toxic or otherwise incompatible with the growth and/or colonization of bacteria and/or fungus (or mold).

Stabilizing Metal Oxide/Hydroxide and Inorganic Mineral Compositions

The aqueous suspension of sparingly soluble basic component useful for coatings preferably comprises sparingly soluble alkali minerals such as one or more inorganic mineral silicates, wollastonite, amorphous magnesium silicate, amorphous calcium silicate, amorphous silica, soluble glass, diatomaceous earth, olivine, and the like. These mixtures are generally unstable when combined in aqueous media, tending to rapidly congeal or increase in viscosity in a short period of time. It has now been found, that one or more of a readily aqueous soluble basic alkali or alkali earth salt of a phosphate, a silicate, or an alkylsiliconate (or arylsiliconate) can effective stabilize the sparingly soluble basic metal oxide and sparingly soluble inorganic mineral composition. It has also been observed that aqueous soluble basic alkali or alkali earth hydroxides can be used, however, potassium hydroxide appears superior in performance to that of sodium hydroxide at equivalent loading. While not to be held to any particular theory, it is believed that potassium cation and/or phosphate anion contributes, in part, to the stabilization of the basic metal oxide/hydroxide and mineral silicate mixture. By providing to the above sparingly soluble basic metal oxide and sparingly soluble inorganic mineral coating composition a readily aqueous soluble basic alkali or alkali earth salt, for example, a potassium salt, a phosphate, a silicate, or an alkylsiliconate, said readily aqueous soluble basic alkali or alkali earth salt of a phosphate, a silicate, or an alkylsiliconate having an aqueous pH between about 9 to about 14, more preferably a pH between about 10 to about 13, effective stabilization is provided, and a stable, useful coating or precursor composition is obtained. The above stabilized metal oxide/hydroxide, inorganic mineral, and soluble basic inorganic salt composition can be used as a coating for surfaces to prevent or eliminate fungal and/or bacterial growth. In one aspect, the amount of readily aqueous soluble basic alkali or alkali earth salt of a phosphate, a silicate, or an alkylsiliconate needed to stabilize the sparingly soluble basic metal oxide and sparingly soluble inorganic mineral composition is about 1 weight percent to about 30 weight percent, or about 2 weight percent to about 20 weight percent, or about 3 weight percent to about 10 weight percent, depending on the loading of oxide and mineral.

In one aspect, the surface of an article can be provided with a basic nature using the coating provide herein, for example, the coating can provide a basic environment of between about pH 9 and about pH 15, between about pH 9.5 and about pH 13, between about pH 10.0 and about pH 12, and between about pH 10 and about pH 11. Such basic environments prevent or inhibit fungal, bacterial and/or microorganism growth or colonization on the surface of the coated article and/or kill or neutralize subsequent contamination of the coated article by such microbes. The coated article can be, for example, a medical article and/or device and/or equipment and/or component, as well as a floor and/or wall surface. After application of the coating composition to a surface or substrate, it "sets" or "sets-up" to a glass-like coating that is securely bonded to the surface or substrate. After set, the coating is resistant to removal by washing, scraping, or during cleaning.

The final pH of the set coating herein disclosed is in the passivation range of steel, e.g., between about pH 9 and about pH 13, between about pH 9.5 and about pH 11.5, between about pH 10.0 and about pH 11.0, between about pH 9.0 and about pH 10.5, between about pH 9.5 and about pH 10.0, between about pH 10.0 and about pH 10.5. Therefore, the coating can offer corrosion protection as well as fungal, bacterial and/or microorganism inhibition, and can further provide hydrophobicity.

In one embodiment, one or more known antifungal and/or antibacterial agents can be included in the composition, provided that the efficacy of the agent is not affected by the basic nature of the composition before, during, or after coating of a substrate. In one aspect, however, no antifungal and/or antibacterial agents are used, the coating having a surface pH effective to prevent or eliminate fungal and/or bacterial growth.

In one aspect, a method of preventing or reducing attachment of Mollusca on a surface is provided. Thus, a surface, for example, a portion or the entirety of a water treatment facility, such as water intake tubes or conduits, can be coated with a coating comprising the precursor formulation of any of the previous embodiments or aspects above, so as to provide the surface, after contacting, a basic environment of at least pH 9, at least pH 9.5, at least pH 10. The surface having a high pH prevents or reduces Mollusca attachment, as most Mollusca prefer an environment having a pH of about 7.2 to 9. While not to be held to any particular theory, it is believed that the high pH surface of the instant coating at least interferes with byssal thread attachment to the basic surface and/or weakens the byssus, and/or is a toxic environment for the Mollusca and/or their larvae or veliger. In one aspect, the Mollusca are fresh water mussels. In one aspect, the Mollusca are zebra mussels or quagga mussels. The present basic coatings provide an alternative to toxic copper, zinc, or tin coatings.

In one aspect, the instant compositions can be configured as an atomizible, sprayable, inorganic composition. The inorganic compositions can be sprayed at a relatively thin thickness. The compositions can hold high solids contents and yet still hold the solids until setting and thus avoiding the solids migrating or dislodging from the point of application, e.g., down a wall, beam, curved surface, or from a ceiling surface. Such spray coated compositions produce high-strength, rapid-setting coatings that provide fungal/bacterial protection suitable for spray coating on metal or non-metal surfaces, for example, medical devices, equipment, components, and the like.

In one aspect, the atomizable composition can comprise an aqueous solution, suspension, or slurry comprising a sparingly aqueous soluble alkaline oxide or alkaline hydroxide represented by $B_{2m}O_m$, $B(OH)_{2m}$, or mixtures thereof, where B is an element of valency 2m (m=1, 1.5, or 2); a sparingly aqueous soluble inorganic silicate, and a soluble basic inorganic salt, adjusted to a pH of between 9-15, and optionally a rheology modifier/suspending agent in an amount capable of providing shear thinning and/or capable of suspending a high solids content for atomization. Optionally, pigments and/or aggregate material can be present in an amount capable of imparting an observable color and/or texture. In one aspect, the alkaline oxide or alkaline hydroxide is an alkali earth metal or transition metal. In another aspect, the alkaline oxide or alkaline hydroxide excludes phosphoric acid or sparingly soluble inorganic phosphate salts, such as those that would provide for a phosphate cement or ceramic. One or more of the components of the instant composition can be wet milled to a size of about 25 to about 150 micron, about 50 to about 100 micron, or about 60 to about 80 micron in average particle size to improve atomization and/or cure/set and/or appearance qualities of the coating.

The above atomizible spray coating can provide a thin, paint-like coating for imparting hydrophobicity and/or fungal/bacterial resistance to metallic and non-metallic surfaces and/or corrosion resistance to corrodible metallic surfaces.

The rheology modifier/suspending agent can be at least one of guar gum, diutan gum, welan gum, and xanthan gum. By using a rheology modifier/suspending agent in an amount capable of providing shear thinning of either the acidic component or the basic component and further capable of suspending a high solids content of the basic component for atomization, excellent paint-like coatings for imparting corrosion resistance to metallic surfaces are obtained.

Examples of Group IV element with at least one carbon covalent bond include silanes, siloxanes, polysilanes, and polysiloxanes. (Poly)silanes and/or (p)olysiloxanes with reactive end-groups, e.g. alkoxy, as self crosslinking anionic or cationic emulsions or low molecular weight oligomers can be used, such as POLON™ silicone or polysiloxane surfactants/sizings, DYNASYLAN™ functionalized silanes/siloxanes and poly- or oligomeric functionalized siloxanes, and the like, in amounts of about 0.1 weight percent to about 20 weight percent, or about 1 weight percent to about 10 weight percent.

In certain aspects of the present disclosure, the metallic surface is that of a transition metal or its alloy, for example, iron, stainless chromium, aluminum, copper, etc. Medical devices, components, equipment, Water may be added to reduce the viscosity thereof, or other types of viscosity reducing agents and/or rheology modifiers may be used. Commercial additives that prevent algae growth may also added to this precursor so that no algae growth occurs during storage of this precursor, however, due to the high pH of the formulation, it is not likely such additives need to be added.

Experimental Section

The following examples are illustrative of the embodiments presently disclosed, and are not to be interpreted as limiting or restrictive. All numbers expressing quantities of ingredients, reaction conditions, and so forth used herein may be understood as being modified in all instances by the term "about." Accordingly, unless indicated to the contrary, the numerical parameters set forth herein may be approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches. Several experimental examples, listed below, were conducted in order to formulate, coat, and demonstrate the attributes of the instant compositions disclosed herein. pH values are provided using pH meters having +/−0.5 accuracy.

The basic component includes, for example, basic oxides, hydroxides and basic minerals. The basic component generally consists of a sparsely soluble oxide. In one aspect, a particle size less than 230 micron of basic component is used. The oxide may be represented by the formula $B^{2m}O_m$ or $B(OH)_{2m}$, where B is a 2m-valent metal; and m is an integer greater than 0. All divalent metal oxides (m=1), and some trivalent metal oxides in reduced state fall into this category of small solubility product constant oxides. Examples of divalent oxides are, but not limited to, magnesium oxide, barium oxide, zinc oxide, calcium oxide, and copper oxide. Examples of trivalent oxides in reduced state are iron oxide (FeO), and manganese oxide (MnO).

In one aspect, a coating is prepared from about 30-50 weight percent sparingly soluble basic metal oxide/hydroxide, about 10 to about 50 weight percent sparingly soluble inorganic silicate, and about 3 to about 30 weight percent an acidic inorganic salt. In one exemplary aspect, about 40 weight percent magnesium hydroxide, about 15-30 weight percent calcium silicate (wollastonite) and about 3-15 weight percent tri potassium phosphate can be used. Applicants have observed that without an effective amount of an aqueous soluble basic inorganic salt, e.g., $K_3PO_4$, the mixture of metal hydroxide and inorganic silicate is unstable after a short time after mixing with aqueous media. For example, the viscosity of the mixture of sparingly soluble basic metal hydroxide and sparingly soluble inorganic silicate goes up significantly with time and cannot be sprayed, or stirred. It has been observed that a loading of soluble basic inorganic salt effective to stabilize the mixture of metal hydroxide and inorganic silicate is about 3 weight percent to about 30 weight percent when the basic organic salt is tripotassium phosphate. While higher loadings of tripotassium phosphate can be used, adjustment of the basic oxide/hydroxide is desirable to avoid slower set up. It has also been observed that a loading of soluble alkali hydroxide effective to stabilize the mixture of sparingly soluble metal hydroxide and inorganic silicate is about 3 weight percent to about 30 weight percent when the soluble basic organic salt is tripotassium phosphate.

In another aspect, a coating is prepared from about 30-50 weight percent sparingly soluble basic metal oxide/hydroxide and about 10 to about 50 weight percent inorganic silicate, and about 3 to about 30 weight percent aqueous soluble basis inorganic salt. Other loadings may be used, for example, for coating horizontal surfaces.

Inorganic Coating Compositions

A range of compositions may be used as the hydrophobic and/or antifungal/antibacterial inhibitor and/or corrosion inhibiting coatings commensurate with the spirit and scope of that disclosed and described herein, the following exemplary, non-limiting example is provided:

| | Weight percent (%) | Comments |
|---|---|---|
| Sample A | Magnesium Hydroxide (~40%) Wollastonite (~22%) Potassium Methyl Siliconate (~20%) Xathum gum (~0.10%) remainder Water | excellent long-term storage stability; excellent resistant to wash-off; excellent microbial resistance; excellent corrosion resistance |
| Sample B | magnesium hydroxide (~38-39%) wollastonite (~20-21%) xanthium gum (0.07%) $K_3PO_4$ (~3.5%) Potassium Methyl siliconate (40% solids) (~9%) remainder water ~27-28% | excellent long-term storage stability; excellent resistant to wash-off; excellent microbial resistance; excellent corrosion resistance |
| Sample C | magnesium hydroxide (~38-39%) wollastonite (~20-21%) xanthium gum (0.07%) $K_3PO_4$ (~3.5%) remainder water ~27-28% | excellent long-term storage stability; poor resistant to wash-off |
| Sample D | Magnesium Hydroxide (~35%) Wollastonite (~19%) self-crosslinking anionic siloxane emulsion (40% solids) (~10%) Xanthan gum (~0.10%) remainder Water | poor long-term storage stability |
| Sample E | Magnesium Hydroxide (~35%) Wollastonite (~19%) silicon emulsion processing aid (~10%) oligomeric or short-chain alkyl and/or phenyl siloxane with hydrolysable alkoxy groups (~1%) $K_3PO_4$ (~4%) Xanthan gum (~0.10%) remainder Water | excellent long-term storage stability; excellent resistant to wash-off; excellent microbial resistance; excellent corrosion resistance |
| Sample F | Magnesium Hydroxide (~42%) Wollastonite (~22%) oligomeric or short-chain alkyl and/or phenyl silane with hydrolysable alkoxy groups (~3%) $K_3PO_4$ (~4%) Xanthan gum (~0.10%) remainder Water | excellent long-term storage stability; excellent resistant to wash-off; excellent microbial resistance; excellent corrosion resistance |
| Sample G | Calcium Hydroxide (~35%) Wollastonite (~22%) Potassium Methyl Siliconate (~20%) Xathum gum (~0.10%) remainder Water | excellent long-term storage stability; excellent resistant to wash-off; excellent microbial resistance; excellent corrosion resistance |
| Sample H | Calcium hydroxide (~30-40%) wollastonite (~20-21%) xanthium gum (0.07%) $K_3PO_4$ (~3.5%) Potassium Methyl siliconate (40% solids) (~9%) remainder water ~27-28% | excellent long-term storage stability; excellent resistant to wash-off; excellent microbial resistance; excellent corrosion resistance |

The above samples was prepared with soluble basic metal salt used at about 0.01 to about 20 weight percent to that of the $Mg(OH)_2$.

The basic nature of the coating and/or monolith was determined by exposing the monolith to a fixed ratio of water/weight sample and measuring the pH. Conventional Ceramicrete and Grancrete materials were used as controls. These control materials have significant amounts of unreacted MgO, which can etch out of a crushed or powder sample, forming MgOH. The test samples chosen form the similar binder MgKPO$_4$. Since the K$_{sp}$ of the binder ceramic is MgKPO$_4$.6H$_2$O is 2.1×10$^{-12}$, the present samples having the basic alkali salt (e.g., K$_3$PO$_4$), which is highly soluble in water, e.g., a solubility of about 90 g per 100 g of water, and an molar excess of the sparingly soluble basic metal oxide/hydroxide, the surface environment of the present samples is greater than the Cermicrete and Grancrete samples.

The results of testing of a number of samples is provided in Table 1. As can be seen from Table 1, the present coatings and monoliths prepared therefrom provided a basic environment of more than pH 10, and greater pH (more basic) than conventional phosphate ceramics/cements, even conventional phosphate ceramics/cements with silicate fillers, which are prepared with essentially an excess of acidic phosphate precursor or with equal molar amounts of acid/base components.

TABLE 1 pH of Samples and Controls

| Sample | pH | Comments |
| --- | --- | --- |
| DI water | 6.62 | |
| CONTROL - Molded Sample Grancrete © Sample Weight Ratio (2:2:2) of (KH$_2$PO$_4$:MgO:Kaolin) | 6.70 | Bulk sample was immersed in the water and pH of water measured after ~1 hr. |
| CONTROL - Molded Sample Grancrete © Sample Weight Ratio (2:2:2) of (KH$_2$PO$_4$:MgO:Wollastonite) | 6.85 | Bulk sample was immersed in the water and pH of water measured after ~1 hr. |
| CONTROL - Molded Ceramicrete (MgO/KH$_2$PO$_4$ + Wollastonite) (Weight ratio = 1:3:6) | 7.72 | Bulk sample was immersed in the water and pH of water measured after ~1 hr. |
| CONTROL - Molded Ceramicrete (Fly ash based), weight ratio = MgO:KH$_2$PO$_4$:Fly ash = 1:3:6 | 7.9 | Bulk sample was immersed in the water and pH of water measured after ~1 hr. |
| Sample A | 9.43 | Bulk sample (metal panel) was immersed in the water and pH of water measured after 1 hr. |

Water Uptake/Water Absorption Testing

For water absorption testing, an ASTM Cement substrate (thickness=~0.5 inch) was used as Control. Comparative sample and test samples of compositions A-D were prepared of 15-20 mils (1 mil=$^1$/$_{1000}$ inches) thickness. Weight gain of the control and each sample over the period of time (one day, 2 days, and 8 days) after submerging in water. Weight gain was converted to weight per unit area (kg/m$^2$). Results are represented as permeability (kg/m$^2$).

Typically, a coating having a water permeability of about 0.3 kg/m$^2$ or less over 24 hours is classified as water impermeable. Samples absorbing water or gaining weight less than 1 kg/m$^2$ are classified as hydrophobic (vapor permeable only). There is another classification which classifies.

As shown in Table 2, Water permeability of the cement control was greater than 5 kg/m$^2$. In comparison, samples A-D had water permeability of less than 1.0 kg/m$^2$. Sample A had a measured water permeability of less than 0.2 kg/m$^2$ and less than 0.15 kg/m$^2$ or about 0.1 kg/m$^2$. Thus, the presently disclosed hydrophobic phosphate ceramic compositions provide water and permeability and/or improved water permeability resistance than conventional ceramic materials and/or coatings.

TABLE 2

Water absorption results for an exemplary embodiment

| Sample | Water absorption (Kg/m$^2$) (day 1; day 2; day 8) |
| --- | --- |
| Comparative Example: Cement-Control Standard ASTM Cement Substrate | 5.58; 5.62; 5.93 |
| Sample A | 0.10; 0.11; 0.11 (day 4) |

Antifungal/Antimicrobial Testing

The purpose of the testing was to evaluate the surface of a treated sample and untreated sample for antimicrobial effectiveness as demonstrated by the JIS Z 2801:2010 test method. Sample A from Table 1 was used for JIS Z 2801 testing. Each sample was tested in triplicate. Test pieces were approximately 50 mm×50 mm.

Procedure: Inoculum was prepared using *Staphylococcus aureus* ATCC #6538P, which was adjusted with a spectrophotometer to a concentration of approximately 2.5-10×10$^8$ Colony-Forming Units per milliliter (CFU/mL). Dilute nutrient broth prepared as described in the test method was used to further dilute the inoculum to 2.5-10×10$^5$ CFU/mL. The untreated sample was tested in triplicate at Time=0 and Time=24 hours to establish organism viability. The treated sample was tested at Time=24 hours. Each sample piece was placed in sterile container and then was inoculated with 0.4 mL of the inoculum. The inoculum was then covered with 40 mm$^2$ piece of sterile plastic (cut from sterile Whirlpak™ bags) in order to spread the inoculum evenly over the sample surface and hold it in place.

The samples were incubated for 24 hours at 35° C. and a relative humidity of at least 90%. At the appropriate time, the samples were placed into a sterile Whirlpak™ bag and 10.0 mL of neutralizing broth was added to the bag. The test pieces were thoroughly massaged in a bag containing the neutralizing broth (SCDLP) to facilitate the release of the inoculum from the sample surface into the neutralizing broth. Serial dilutions of the neutralizing broth containing the inoculum were plated. All plates were incubated at 35° C. for 24-48 hours. After incubation, bacterial colonies were counted and recorded.

Test Results are summarized in Table 3 below. An untreated MSL plastic control recovered an appropriate amount of organism at Time=0 and Time=24 to confirm organism viability. The number of viable bacteria in the test inoculum was 1.3×10$^5$ CFU/mL. The number of viable bacteria in the test inoculum was 5.9×10$^5$ CFU/mL for *Staphylococcus aureus* and 4.7×105 CFU/mL for *Escherichia coli*. This is the initial number of bacteria placed onto to the sample surface for testing. This is the initial number of bacteria placed onto to the sample surface for testing. The value of the antimicrobial activity was calculated according to the formula (I) listed below and recorded as log reduction.

$$R=(Ut-Uo)-(At-Uo)=Ut-At \qquad (I)$$

Where, R: antimicrobial activity; Uo: average of logarithm numbers of viable bacteria from untreated sample at Time=0; Ut: average of logarithm numbers of viable bacteria from untreated sample at Time=24 h; and At: average of logarithm numbers of viable bacteria from treated sample at Time=24 h.

TABLE 3

*Staphylococcus aureus* inhibition Testing of coatings disclosed herein

| | |
|---|---|
| Uo: Average of logarithm numbers of viable bacteria from untreated control at Time = 0 | 4.02 |
| $U_t$: Average of logarithm numbers of viable bacteria from control sample at Time = 24 h | 4.60 |
| $A_t$: Average of logarithm numbers of viable bacteria from Sample A at Time = 24 h | −0.0023 |

According to the standard, an antibacterial product is determined to have antibacterial effectiveness when the antibacterial activity (R) is 2.0 or more. The sample coated with Sample A disclosed herein had an R value of 4.60, indicating a percent reduction of viable bacteria of 99.998 percent or excellent antibacterial activity against *S. aureus*.

Against *Escherichia coli* ATCC#8739, similar improvement was observed for the instant coating prepared from the composition of Sample A. Thus, as summarized in Table 4,

TABLE 4

*Escherichia coli* inhibition Testing of coatings disclosed herein

| | |
|---|---|
| Uo: Average of logarithm numbers of viable baeteria from untreated control at Time = 0 | 3.93 |
| $U_t$: Average of logarithm numbers of viable bacteria from control sample at Time = 24 h | 5.23 |
| $A_t$: Average of logarithm numbers of viable bacteria from BC I at Time - 24 h | −0.20 |
| $A_t$: Average .of logarithm numbers of viable bacteria from ECH at Time = 24 h | 0.14 |
| $.1_1$; Average of logarithm numbers of viable bacteria froM EC .at Time = 24 h | 3.84 |

For comparison, a conventional phosphate ceramic sample (without a Group IV-hydrocarbon bond component) was found to have an antibacterial activity (R) of about 1.39 or a percent reduction of viable bacteria of only 95 percent.

Thus, the aforementioned compositions and coatings disclosed herein are effective in inhibiting and preventing *E. coli* and other hospital-related bacteria, as *E. coli* and other bacteria and/or fungus and are superior to existing compositions of silicate composition without the Group IV-hydrocarbon bond component.

What is claimed:

1. A precursor composition consisting essentially of:
    water, and a slurry or suspension of the following:
    at least one sparingly soluble metal oxide/hydroxide having a solubility constant of $10^{-4}$ or smaller in aqueous media;
    at least one sparingly soluble inorganic mineral having a solubility constant of $10^{-4}$ or smaller in aqueous media;
    at least one soluble basic inorganic salt having a solubility constant of $10^{-3}$ or greater in aqueous media; and
    at least one hydrophobic agent, wherein the hydrophobic agent is a mono-, di-, or tri-alkyl siliconate salt in an amount capable of providing hydrophobicity.

2. The composition of claim 1, wherein the at least one sparingly soluble metal oxide/hydroxide is at least one of magnesium oxide or magnesium hydroxide.

3. The composition of claim 1, wherein the at least one sparingly soluble metal oxide/hydroxide is at least one of calcium oxide, calcium hydroxide, barium oxide, zinc oxide, copper oxide, or hydroxides thereof.

4. The composition of claim 1, wherein the at least one sparingly soluble inorganic mineral is one or more of an inorganic mineral silicate, wollastonite, talc, amorphous magnesium silicate, amorphous calcium silicate, diatomaceous earth, aluminosilicate, olivine, calcined kaolin, mullite, colloidal silica, silicon dioxide, or amorphous silicon dioxide.

5. The composition of claim 1, wherein the at least one soluble basic inorganic salt is one or more of an alkali metal or alkali earth metal salt of a phosphate or a silicate.

6. The composition of claim 1, wherein the at least one soluble basic inorganic salt is potassium phosphate salt ($K_3PO_4$).

7. The composition of claim 1, wherein the at least one soluble basic inorganic salt is potassium hydroxide.

8. The composition of claim 1, wherein the hydrophobic agent is a potassium salt of the mono-, di-, or tri-alkyl siliconate.

\* \* \* \* \*